United States Patent [19]
Metzger et al.

[11] Patent Number: 5,985,264
[45] Date of Patent: Nov. 16, 1999

[54] IL-12 STIMULATION OF NEONATAL IMMUNITY

[75] Inventors: Dennis W. Metzger, Sylvania; Bernard P. Arulanandam, Toledo, both of Ohio

[73] Assignee: The Medical College of Ohio, Toledo, Ohio

[21] Appl. No.: 09/035,593

[22] Filed: Mar. 5, 1998

[51] Int. Cl.[6] .......................... A61K 45/05; A61K 39/00
[52] U.S. Cl. ................... 424/85.2; 424/85.4; 424/184.1; 424/191.1; 424/204.1; 424/234.1; 424/264.1; 424/269.1; 530/350
[58] Field of Search .................................. 424/85.2, 58.4, 424/184.1, 191.1, 204.1, 234.1, 264.1; 530/350

[56] References Cited

PUBLICATIONS

Mancuso et al, Infection And Immunity, Sep. 1997, vol. 65, No. 9, pp. 3731–3735.
Gerosa et al, The Journal of Experimental Medicine, Jun. 1996, vol. 183, pp. 2559–2569.
Wu et al, The Journal of Immunology, Aug. 1993, vol. 151, No. 4, pp. 1938–1949.
Ridge, J.P., et al., "Neonatal Tolerance Revisited: Turning on Newborn T Cells with Dendritic Cells," *Science*, 271:1723–1726 (1996).
Mond, J.J., et al., "T Cell–Independent Antigens Type 2," *Annu. Rev. Immunol.*, 13:655–692 (1995).
Sarzotti, M., et al., "Induction of Protective CTL Responses in Newborn Mice by a Murine Retrovirus," *Science*, 271:1726–1728 (1996).
Forsthuber, T., et al., "Induction of $T_H1$ and $T_H2$ Immunity in Neonatal Mice," *Science*, 271:1728–1730 (1996).
Adkins, B., et al., "Developmental Regulation of IL–4, IL–2, and IFN–y Production by Murine Peripheral T Lymphocytes," *J. Immunol.*, 151(12):6617–6626 (1993).
Barrios, C., et al., "Partial Correction of the TH2/TH1 Imbalance in Neonatal Murine Responses to Vaccine Antigens through Selective Adjuvant Effects," *Eur. J. Immunol.*, 26:266–2670 (1996).
Macatonia, S.E., et al., "Dendritic Cells Produce IL–12 and Direct the Development of Th1 Cells from Naive $CD4^+T$ Cells," *J. Immunol.*, 154:5071–5079 (1995).
Steinman, R.M., et al., "Identification of a Novel Cell Type in Peripheral Lymphoid Organs of Mice," *J. Exp. Med.*, 139:1431–1445 (1974).
Finkelman, F.D., et al., "IFN–y Regulates the Isotypes of Ig Secreted During In Vivo Humoral Immune Responses," *J. Immunol.*, 140(4):1022–1028 (1988).
Snapper, C.M., et al., "IFN–y Stimulates IgG2a Secretion by Murine B Cells Stimulated with Bacterial Lipopolysaccharide," *J. Immunol.*, 140(7):2121–2127 (1988).
Shu, U., et al., "Interleukin 12 Exerts a Differential Effect on the Maturation of Neonatal and Adult Human $CD45R0^-CD4$ T Cells," *J. Clin. Invest.*, 94:1352–1358 (1994).
Sornasse, T., et al., "Differentiation and Stability of T Helper 1 and 2 Cells Derived from Naive Human Neonatal $CD4^+T$ Cells, Analyzed at the Single–cell Level," *J. Exp. Med.*, 184:473–483 (1996).
Martinez, X., et al., "DNA Immunization Circumvents Deficient Induction of T Helper Type 1 and Cytotoxic T Lymphocyte Responses in Neonates and During Early Life," *Proc. Natl. Acad. Sci. USA*, 94:8726–8731 (1997).
Bot, A., et al., "Induction of Humoral and Cellular Immunity Against Influenza Virus by Immunization of Newborn Mice with a Plasmid Bearing a Hemagglutinin Gene," *International Immunol.*, 9(11):1641–1650 (1997).
Chu, R.S., et al., "CpG Oligodeoxynucleotides Act as Adjuvants that Switch on T Helper 1 (Th1) Immunity," *J. Exp. Med.*, 186(10):1623–1631 (1997).
Adkins, B., et al., "Up–Regulation of Murine Neonatal T Helper Cell Responses by Accessory Cell Factors," *J. Immunol.*, 153:3378–3385 (1994).
Coutinho, G.C., et al., "Developmental Shift in the Patterns of Interleukin Production in Early Post–natal Life," *Eur. J. Immunol.* 24:1858–1862 (1994).
Early, E.M. and Reen, D.J., "Antigen–Independent Responsiveness to Interleukin–4 Demonstrates Differential Regulation of Newborn Human T Cell," *Eur. J. Immunol.*, 26:2885–2889 (1996).
Kobayashi, M., et al., "Identification and Purification of Natural Killer Cell Stimulatory Factor (NKSF), A Cytokine with Multiple Biologic Effects on Human Lymphocytes," *J. Exp. Med.* 170:827–845 (1989).
Barrios, C., et al., "Neonatal and Early Life Immune Responses to Various Forms of Vaccine Antigens Qualitatively Differ from Adult Responses: Predominance of a Th2–biased pattern which Persists after Adult Boosting," *Eur. J. Immunol.* 26:1489–1496 (1996).
Van Regenmortel, M., "Searching for Safer, More Potent, Better–argeted Adjuvants," *ASM News*, 63:136–139 (1996).
Buchanan, J.M., et al., "Biological Properties and Potential Clinical Applications of Interleukin 12," *Int'l J. Ped. Hemat./Oncol.*, 3:123–131 (1996).
Trinchieri, G., "Interleukin–12: A Proinflammatory Cytokine with Immunoregulatory Functions that Bridge Innate Resistance and Antigen–Specific Adaptive Immunity," *Annu. Rev. Immunol.*, 13:251–276 (1995).
Donckier, V., et al., "IL–12 prevents neonatal induction of transplantation tolerance in mice," *Eur. J. Immunol.*, 28(4):1426–1430 (1998).

*Primary Examiner*—Frank C. Eisenschenk
*Assistant Examiner*—Ali R. Salimi
*Attorney, Agent, or Firm*—Hamilton, Brook, Smith & Reynolds, P.C.

[57] ABSTRACT

The present invention relates to a method of inducing a Th1-like response against a pathogen in a neonatal host, which comprises administering to the neonatal host an effective amount of IL-12 and an antigen of the pathogen. Also encompassed by the present invention is a method of overcoming suppression of interferon-γ (IFN-γ) expression in a neonatal host due to exposure of the neonatal host to a pathogen or an antigen, which comprises administering to the neonatal host an effective amount of IL-12 and the antigen. The present invention also relates to a method of enhancing the cytokine expression against or in response to a pathogen in a neonatal host, which comprises administering to the neonatal host an effective amount of IL-12 and an antigen of the pathogen.

7 Claims, 7 Drawing Sheets

IL-12 STIMULATION OF NEONATAL IMMUNITY

GOVERNMENT SUPPORT

The invention was supported, in whole or in part, by a grant R21 AI38380 from the National Institutes of Health. The Government has certain rights in the invention.

BACKGROUND OF THE INVENTION

The neonatal immune system has been traditionally thought to be immature and functionally dependent upon maternal antibodies for protection against pathogenic organisms. In fact, Burnet, F. M. and Fenner, F., Macmillan, Melbourne, *The Production of Antibodies*, 102–105 (1949) proposed that exposure of the human neonate to antigens including infectious agents, would induce a state of specific immunological tolerance to those antigens. Medawar and colleagues (Billingham, R. E. et. al., *Nature*, 172:603 (1952)) later provided experimental evidence for this hypothesis by showing that newborn mice exposed to foreign white blood cells would accept foreign tissues from the same donor as adults.

Effective methods for inducing immunity to pathogens in the neonatal immune system are needed.

SUMMARY OF THE INVENTION

The present invention relates to a method of enhancing (e.g., inducing) an immune response in a neonatal host. In one embodiment, the present invention relates to a method of inducing an immune response to a pathogen (one or more) in a neonatal host (mammalian, including human), which comprises administering to the host an effective amount of IL-12 and an antigen (e.g., protein, carbohydrate, lipid, recombinant DNA, whole organism, toxin, organic molecule) of the pathogen. In another embodiment, the present invention relates to a method of enhancing an immune response to a pathogen in a neonatal host, which comprises administering to the host an effective amount of IL-12 and an antigen of the pathogen. As described herein, the immune response induced or enhanced in the neonatal host can be, for example, a cytokine immune response and/or a humoral immune response (e.g., antigen-specific).

The present invention also relates to a method of inducing a cytokine response against a pathogen in a neonatal host, which comprises administering to the neonatal host an effective amount of IL-12 and an antigen of the pathogen.

Also encompassed by the present invention is a method of overcoming suppression of interferon-γ (IFN-γ) expression in a neonatal host due to exposure of the neonatal host to a pathogen or an antigen, which comprises administering to the neonatal host an effective amount of IL-12 and the antigen of the pathogen.

The present invention also relates to a method of enhancing the cytokine expression against or in response to a pathogen in a neonatal host, which comprises administering to the neonatal host an effective amount of IL-12 and an antigen of the pathogen.

Methods and compositions for inducing an immune response to pathogens in a neonatal host are needed. The present invention provides for methods of enhancing immunity and inducing memory for protective responses in neonatal hosts.

DETAILED DESCRIPTION OF THE INVENTION

Figure 1A:
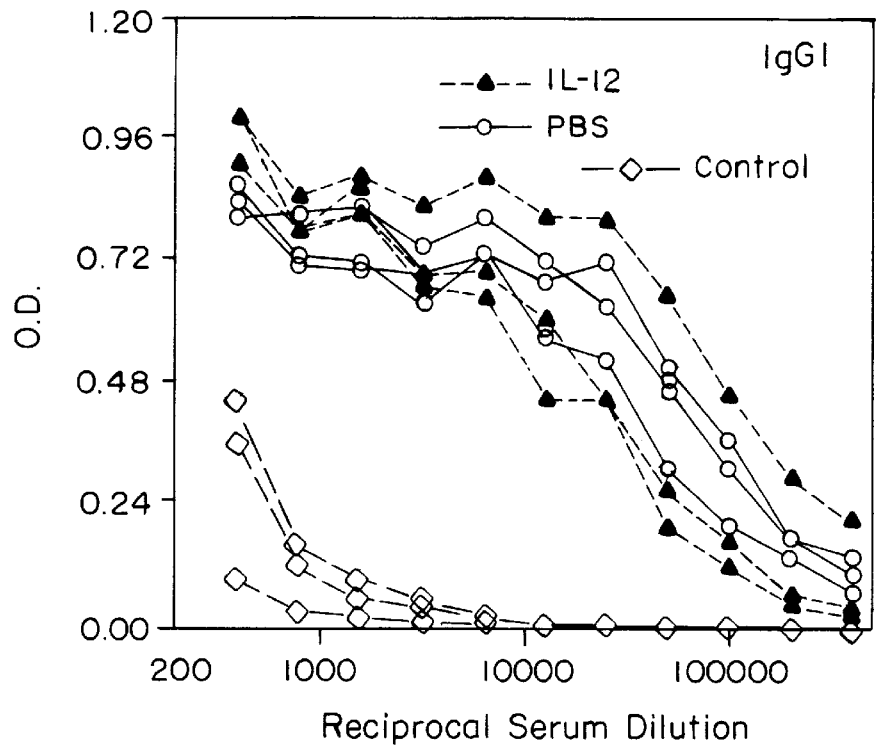
FIGS. 1A–1C are graphs of reciprocal serum dilution versus optical density (O.D.) showing the effects of IL-12 on serum anti-dinitrophenyl hapten (DNP) levels after neonatal DNP conjugated to ovalbumin (DNP-OVA) priming +/–IL-12 in mice injected with DNP-OVA in incomplete Freund's adjuvant (IFA) plus IL-12 (closed triangles), DNP-OVA in either IFA plus phosphate buffered saline (PBS) vehicle (open circles) or PBS vehicle only (open squares); each line represents binding of serum from an individual mouse; the mice were then challenged after 5–6 weeks of age with DNP-OVA in complete Freund's adjuvant (CFA) and the sera were tested 7 days later for anti-DNP antibodies by ELISA; the differences in binding between mice primed with DNP-OVA and IL-12 and those primed with DNP-OVA and PBS were significant at $p<0.05$ for IgG2a and IgG2b.

As demonstrated herein, administration of IL-12 to a neonatal host enhances (e.g., induces) immunity early in life and induces memory for protective responses. Thus, the present invention relates to methods of enhancing immunity to a pathogen and/or antigen in a neonatal host. In one embodiment, the present invention relates to a method of inducing an immune response to a pathogen in a neonatal host, which comprises administering to the neonatal host an effective amount of IL-12 and an antigen of the pathogen. In another embodiment, the present invention relates to a method of enhancing an immune response to a pathogen in a neonatal host, which comprises administering to the neonatal host an effective amount of interleukin-12 and an antigen of the pathogen.

As used herein, the terms "enhance" and/or "enhancing" refer to the strengthening (augmenting) of an existing immune response to a pathogen in a neonatal host. The term also refers to the initiation of (initiating, inducing) an immune response to a pathogen in a neonatal.

An antigen (one or more) for use in the present invention includes, but is not limited to, proteins or fragments thereof (e.g., proteolytic fragments), peptides (e.g., synthetic peptides, polypeptides), glycoproteins, carbohydrates (e.g., polysaccharides), lipids, glycolipids, hapten conjugates, recombinant DNA, whole organisms (killed or attenuated) or portions thereof, toxins and toxoids (e.g., tetanus, diphtheria, cholera) and/or organic molecules. Particular examples of antigens for use in the present invention include hemagglutinin and neuraminidase obtained or derived from the influenza virus.

The antigen can be obtained or derived from a variety of pathogens or organisms, such as bacteria (e.g., bacillus, Group B streptococcus, Bordetella, Listeria, *Bacillus anthracis, S. pneumoniae, N. meningiditis, H. influenza*), viruses (e.g., hepatitis, measles, poliovirus, human immunodeficiency virus, influenza virus, parainfluenza virus, respiratory syncytial virus), mycobacteria (*M. tuberculosis*), parasites (Leishmania, Schistosomes, Tranpanosomes, toxoplasma, pneumocystis) and fungi (e.g., Candida, Cryptococcus, Coccidiodes, Aspergillus), against which an immune response is desired in a host. The antigen of a pathogen can be obtained using skills known in the art. For example, the antigen can be isolated (purified, essentially pure) directly from the pathogen, derived using chemical synthesis or obtained using recombinant methodology. In addition, the antigen can be obtained from commercial sources. A suitable antigen for use in the present invention is one that includes at least one B and/or T cell epitope (e.g., T helper cell or cytolytic T cell epitope). Other suitable antigens useful in the compositions of the present invention can be determined by those of skill in the art.

IL-12 is a recently characterized heterodimeric cytokine that has a molecular weight of 75 kDa and is composed of disulfide-bonded 40 kDa and 35 kDa subunits. It is produced by antigen presenting cells such as macrophages, and binds to receptors on activated T, B and NK cells (Desai, B. B., et al., *J. Immunol.*, 148:3125–3132 (1992); Vogel, L. A., et al., *Int. Immunol.*, 8:1955–1962 (1996)). It has several effects including 1) enhanced proliferation of T cells and NK cells, 2) increased cytolytic activities of T cells, NK cells, and macrophages, 3) induction of IFN-γ production and to a lesser extent, TNF-α and GM-CSF, and 4) activation of TH1 cells (Trinchieri, G., et al., *Blood*, 84:4008–4027 (1994). IL-12 has been shown to be an important costimulator of proliferation in Th1 clones (Kennedy et al., *Eur. J. Immunol.* 24:2271–2278, 1994) and leads to increased production of IgG2a antibodies in serum (Morris, S. C., et al., *J. Immunol.* 152:1047–1056 (1994); Germann, T. M., et al., *Eur. J. Immunol.*, 25:823–829 (1995); Sher, A., et al., *Ann. N.Y. Acad. Sci.*, 795:202–207 (1996); Buchanan, J. M., et al., *Int. Immunol.*, 7:1519–1528 (1995); Metzger, D. W. et al., *Eur.* *J. Imunol.*, 27:1958–1965 (1997)). Administration of IL-12 can also temporarily decrease production of IgG1 antibodies (Morris, S. C., et al., *J. Immunol.* 152:1047–1056 (1994); McKnight, A. J., *J. Immunol.* 152:2172–2179 (1994); Buchanan, J. M., et al., *Int. Immunol.*, 7:1519–1528 (1995)), indicating suppression of the Th2 response. The purification and cloning of IL-12 are disclosed in PCT publication nos. WO 92/05256 and WO 90/05147, and in European patent publication no. 322,827 (identified as "CLMF"). All of the above effects were observed in adult animals.

As used herein, "interleukin-12" and "IL-12" refer to interleukin 12 protein, its individual subunits, multimers of its individual subunits, functional fragments of IL-12, and functional equivalents and/or analogues of "interleukin-12" and "IL-12". As defined herein, functional fragments of IL-12 are fragments which, for example, when administered with an antigen, induce an immune response to the antigen in a neonatal host. As also defined herein, functional fragments or equivalents of "interleukin-12" and "IL-12" include modified IL-12 protein such that the resulting IL-12 product has activity similar to the IL-12 described herein (e.g., the ability to induce an immune response to an antigen, when administered with the antigen, in a neonatal host). Functional equivalents or fragments of "interleukin-12" also include nucleic acid sequences (e.g., DNA, RNA) and portions thereof, which encode a protein or peptide having the IL-12 function or activity described herein (e.g., the ability to induce an immune response to an antigen, when administered with the antigen, in a neonatal host). In addition, the term includes a nucleotide sequence which through the degeneracy of the genetic code encodes a similar peptide gene product as IL-12 and has the IL-12 activity described herein. For example, a functional equivalent of "interleukin-12" and "IL-12" includes a nucleotide sequence which contains a "silent" codon substitution (e.g., substitution of one codon encoding an amino acid for another codon encoding the same amino acid) or an amino acid sequence which contains a "silent" amino acid substitution (e.g., substitution of one acidic amino acid for another acidic amino acid).

IL-12 suitable for use in the methods of the present invention can be obtained from a variety of sources or synthesized using known skills. For example, IL-12 can be purified (isolated, essentially pure) from natural sources (e.g., mammalian, such as human sources), produced by chemical synthesis or produced by recombinant DNA techniques. In addition, the IL-12 for use with the present invention can be obtained from commercial sources.

An effective amount of IL-12 is administered in the methods of the present invention which is an amount that enhances an immune response to an antigen in a neonatal host. In particular, "an effective amount of IL-12" is an amount such that when administered to a neonatal host, it results in a general upregulation of immunity in the neonatal host relative to the immunity of a neonatal host when an effective amount of IL-12 is not administered to the neonatal host; and, when administered with an antigen, it induces and/or enhances an immune response to the antigen in the neonatal host relative to the immune response to the antigen in a neonatal host when an effective amount of IL-12 is not administered to the neonatal host. That is, an "effective amount" of IL-12 is an amount that upregulates immunity in a neonatal host, and/or when administered with an antigen it induces and/or enhances an immune response to an antigen in a neonatal host, relative to the immune response to the antigen if IL-12 is not administered to the neonatal host.

As used herein, "neonatal host" is a mammalian host, such as a primate (e.g., human), murine, feline, canine, bovine or porcine host. In addition, the term includes a newborn host and a host whose period of life extends from about 7 months prior to birth to about 2 years after birth. Several vaccines are ineffective until the age of about two years. In one embodiment, a neonatal host refers to a host whose period of life extends from about 3 months prior to birth to about 2 years after birth. In another embodiment, a neonatal host refers to a host whose period of life extends from about 1 week prior to birth to about 1 year after birth. In the methods of the present invention, the IL-12 or, the IL-12 and antigen, can be administered directly or indirectly to the neonatal host. That is, the IL-12 or, the IL-12 and antigen, can be administered directly to the neonatal host in utero or after birth. Alternatively, the IL-12 or, the IL-12 and antigen, can be administered indirectly, wherein the composition is administered to a pregnant mother, crosses the placenta and is delivered to the neonatal host indirectly.

The IL-12 and/or the antigen can be administered as a prophylactic vaccine or a therapeutic vaccine. That is, the IL-12 can be administered either before (to prevent) or after (to treat) the effects of a pathogen which has appeared and/or manifested in a neonatal host. Thus, the IL-12 and/or antigen can be administered to a neonatal host who either exhibits the disease state caused by a pathogen from which the antigen is obtained or derived, or does not yet exhibit the disease state caused by a pathogen from which the antigen is obtained or derived. Thus, the IL-12 and/or antigen can be administered to a neonatal host either before or after the disease state is manifested in the neonatal host and can result in prevention, amelioration, elimination or a delay in the onset of the disease state caused by the pathogen from which the antigen is obtained or derived.

The IL-12 and/or the antigen can be administered to a host in a variety of ways. The routes of administration include intradermal, transdermal (e.g., slow release polymers), intramuscular, intraperitoneal, intravenous, subcutaneous, oral, epidural and intranasal routes. Any other convenient route of administration can be used, for example, infusion or bolus injection, or absorption through epithelial or mucocutaneous linings. In addition, the IL-12 and/or antigen can be administered together with other components or biologically active agents, such as adjuvants (e.g., alum), pharmaceutically acceptable surfactants (e.g., glycerides), excipients (e.g., lactose), liposomes, carriers, diluents and vehicles. If desired, certain sweetening, flavoring and/or coloring agents can also be added.

Further, the IL-12 and/or antigen, in the embodiment wherein the antigen is a protein (peptide), can be administered by in vivo expression of polynucleotides encoding such into a neonatal host. For example, the IL-12 or the antigen can be administered to a neonatal host using a live vector, wherein the live vector containing IL-12 and/or antigen nucleic acid sequences is administered under conditions in which the IL-12 and/or antigen are expressed in vivo. A neonatal host can also be injected with a vector which encodes and expresses an antigen in vivo in combination with IL-12 protein or peptide, or in combination with a vector which encodes and expresses the IL-12 protein in vivo. Alternatively, a neonatal host can be injected with a vector which encodes and expresses IL-12 in vivo in combination with an antigen in peptide or protein form, or in combination with a vector which encodes and expresses an antigen in vivo. A single vector and the IL-12 protein are also useful in the methods of the present invention.

Several expression vector systems are available commercially or can be reproduced according to recombinant DNA and cell culture techniques. For example, vector systems such as the yeast or vaccinia virus expression systems, or virus vectors can be used in the methods and compositions of the present invention (Kaufman, R. J., *A J. of Meth. in Cell and Molec. Biol.*, 2:221–236 (1990)). Other techniques using naked plasmids or DNA, and cloned genes encapsulated in targeted liposomes or in erythrocyte ghosts, can be used to introduce IL-12 polynucleotides into the host (Freidman, T., *Science*, 244:1275–1281 (1991); Rabinovich, N. R., et al., *Science*, 265:1401–1404 (1994)). The construction of expression vectors and the transfer of vectors and nucleic acids into various host cells can be accomplished using genetic engineering techniques, as described in manuals like *Molecular Cloning and Current Protocols in Molecular Biology*, which are hereby incorporated by reference, or by using commercially available kits (Sambrook, J., et al., *Molecular Cloning*, Cold Spring Harbor Press, 1989; Ausubel, F. M., et al., *Current Protocols in Molecular Biology*, Greene Publishing Associates and Wiley-Interscience, 1989).

As described herein, administration of IL-12 and an antigen to a neonatal host elicits or enhances an immune response in the recipient neonatal host. In one embodiment, the present invention relates to a method of inducing a cytokine (e.g.,Th1-like) response against a pathogen in a neonatal host, which comprises administering to the neonatal host an effective amount of IL-12 and an antigen of the pathogen. In another embodiment, the present invention relates to a method of overcoming suppression of interferon-$\gamma$ expression in a neonatal host due to exposure of the neonatal host to a pathogen or an antigen, which comprises administering to the neonatal host an effective amount of IL-12 and the antigen. Also encompassed by the present invention is a method of enhancing the cytokine expression against or in response to a pathogen in a neonatal host, which comprises administering to the neonatal host an effective amount of interleukin-12 and an antigen of the pathogen.

For example, in neonatal hosts treated with IL-12 and antigen an immune response is elicited wherein expression of IFN-$\gamma$ and/or IL-10 is enhanced. In addition, a humoral immune response (e.g., antigen-specific) is induced and/or enhanced in a neonatal host treated with IL-12 and antigen. In one embodiment, the humoral immune response produced by administration of IL-12 and an antigen results in enhanced levels of total antibody in the recipient neonatal host compared to a neonatal host which does not receive IL-12 and the antigen. In a particular embodiment, the antibody response produces specific IgG1, IgG2a and/or IgG2b in the recipient neonatal host.

In the methods of enhancing an immune response to an antigen in a neonatal host, an effective amount of IL-12 is administered to the host, which is an amount that enhances an immune response to the antigen in the neonatal host and results in the improved condition of the neonatal host (i.e., the disease or disorder caused by the presence of the pathogen from which the antigen is obtained or derived, is prevented, eliminated or diminished). The amount of IL-12 used to induce or enhance an immune response to an antigen in a neonatal host will vary depending on a variety of factors, including the size, age, body weight, general health, sex and diet of the host, and the time of administration, duration or particular qualities of the disease state. Suitable dose ranges of IL-12 are generally about 0.5 $\mu$g to about 150 $\mu$g per kg body weight. In one embodiment, the dose range is from about 2.75 $\mu$g to about 100 $\mu$g per kg body weight. In another embodiment, the dose range is from about 5 $\mu$g to about 50 $\mu$g per kg body weight. Effective dosages may be extrapolated from dose-response curves derived in vitro or in animal model test systems.

In the methods of the present invention, an effective amount of IL-12 is administered in combination with an antigen. That is, the IL-12 is administered at a time closely related to immunization of the neonatal host with an antigen, so that an immune response to the antigen is induced or enhanced in the neonatal host relative to the immunization of a neonatal host in which IL-12 is not administered. Thus, the IL-12 can be administered prior to, preferably just prior to, immunization; at the time of immunization (i.e., simultaneously); or after immunization (subsequently). In addition, the IL-12 can be administered prior to immunization with the antigen followed by subsequent administrations of IL-12 after immunization with the antigen.

As demonstrated herein, administration of IL-12 to newborn mice redirects their cytokine expression and primes the animals for enhanced antibody responses as adults. Therefore, inoculation of IL-12 into neonates is a useful means for enhancing immunity early in life and helping induce memory for protective responses in a neonate.

Recent work showed that newborn mice could be primed to recognize foreign antigens as long as priming was performed under the appropriate conditions. Matzinger and colleagues (Ridge, J. E. et. al., *Science*, 271:1723–1726 (1996)) found that the nature of the antigen-presenting cell determined whether the outcome of antigen exposure was neonatal tolerance or immunization. Specifically, they found that providing dendritic cells to newborn mice allowed them to be primed rather than tolerized to allogeneic spleen cells. The recent success of the *H. influenzae* conjugate vaccine has demonstrated that nonresponsiveness can be overcome if appropriate help is provided to neonatal B cells, but vaccine conjugates against other TI antigens have not yet become available. Furthermore, anti-polysaccharide responses induced with conjugate vaccines still maintain many of the characteristics of the TI responses (Mond, J. J. et. al., *Annu. Rev. Immunol.*, 13:655–692 (1995)). Sarzotti, M. et. al., *Science*, 271:1726–1728 (1996) reported that exposure of neonates to small amounts of antigen which presumably did not overwhelm the animal's own dendritic cells, actually led to immunity rather than tolerance. Lehmann and colleagues (Forsthuber, T. et. al., *Science*, 271:1728–1730 (1996)) demonstrated that neonatal "tolerization" to protein antigens actually induces immune deviation and causes restriction to Th2 responses which are characterized by expression of IL-4, IL-5, IL-6, and IgG1 antibody. Establishment of Th2 memory would thus appear to induce tolerance to foreign grafts since Th2 responses suppress specific Th1 responses involving IFN-γ production and activated cytotoxic T cells and NK cells, the primary mechanisms thought to be responsible for graft rejection. Others have similarly reported that the newborn immune system displays polarized expression of Th2 cytokines and antibody isotypes (Adkins, B. et. al., *J. Immunol.*, 151:6617–6626 (1993); Coutinho, G. et. al., *Eur. J. Immunol.*, 24:1858–1862 (1994); Early, E. M. and Reen, D. J., *Eur. J. Immunol.*, 26:2885–2889 (1996); Barrios, C. et. al., *Eur. J. Immunol.*, 26:1489–1496 (1996) and Barrios, C. et. al., *Eur. J. Immunol.*, 26:2666–2670 (1996)).

The primary inducer of the Th1 pathway is IL-12 which is a 70 kD heterodimeric protein that has pleiotrophic effects on immunity. It has been shown that IL-12 1) enhances proliferation of T cells and NK cells, 2) increases cytolytic activities of T cells, NK cells, and macrophages, 3) activates Th1 cells, and 4) induces production of IFN-γ and other cytokines [see recent reviews by Trinchieri G., *Blood*, 84:4008–4027 (1994) and Buchanan, J. M. et. al., *Int. J. Pediat. Hematol. Oncol.*, 3:123–131 (1996)).

As described herein, newborns are deficient in IL-12 expression in peripheral lymphoid organs. Furthermore, administration or recombinant IL-12 redirects the newborn immune system towards a Th1-type cytokine profile and enhances development of antibody memory responses.

In adults, IL-12 stimulates the proliferation of T cells and NK cells, increases the cytolytic activity of $CD8^+$ T cells and NK cells, and augments the production of IFN-γ and other cytokines (Trinchieri, G., *Res. Immunol.*, 146:423–431 (1995); Trinchieri, G., *Immunol. Today*, 14:335–338 (1993)). The observed deficiency of neonates in IL-12 expression could thus be responsible for poor responsiveness and a bias towards Th2 responses. The reason for this deficiency is unknown, although it could be related to the fact that dendritic cells are a major source of IL-12 (Macatonia, S. E., et al., *J. Immunol.*, 154:5071–5079 (1995) and that the number of dendritic cells in neonates is very low. In fact, dendritic cells do not reach adult levels until 3–4 weeks of age (Steinman, R., et al., *J. Exp. Med.*, 139:1431–1445 (1974). The importance of dendritic cells has been underscored by the findings of Matzinger and colleagues (Ridge, P. G., et al., *Science*, 271:1723–1726 (1996)) who demonstrated that providing dendritic cells to newborn animals allowed them to become immunologically responsive. It is possible that one mechanism for IL-12's ability to enhance neonatal immunity involves replacing the in vivo requirement for dendritic cells.

Despite the lack of IL-12 in the periphery, neonatal mice were clearly able to respond to injections of exogenous IL-12 with increased expression of IFN-γ and IL-10. In contrast, no detectable levels of IFN-γ transcripts were observed in mice receiving antigen or vehicle only. IFN-γ is a potent immunoregulator of Th subset effector functions and plays a pivotal role in activation of macrophages and isotype switching of B cells to IgG2a production, effects which are characteristic of Th1 immune responses (Snapper, C. M., et al., *Science*, 236:944–947 (1987); Finkelman, F. D., et al., *J. Immunol.*, 140:1022–1027 (1988); Snapper, C. M., et al., *J. Immunol.*, 140:2121–2127 (1988)). Similarly, another important regulator of the T cells response is IL-10 which is induced by IL-12 (Gerosa, F., et al., *J. Exp. Med.*, 183:2559–2569 (1996); Sher, A., et al., *Ann. N.Y. Acad. Sci.*, 795:202–207 (1996); Meyaard, L., et al., *J. Immunol.*, 156:2776–2782 (1996); Daftarian, P. M., et al., *J. Immunol.*, 157:12–20 (1996)) and thought to be involved in a negative feedback mechanism designed to modulate the Th1 pathway and dampen the effects of IFN-γ, an idea that is fully compatible with the results described herein. While enhancing IFN-γ and IL-10 production, IL-12 had no effects on neonatal IL-4 and IL-5 expression. These results contrast with those of Shu et al. (Shu, U., et al., *J. Clin. Invest.*, 94:1352–1358 (1994)) and Sornasse et al. (Sornasse, T., et al., *J. Exp. Med.*, 184:473–483 (1996)) who found that in vitro treatment of human neonatal T cells with IL-12 stimulated both IFN-γ and IL-4 expression. The reasons for the differing results are unknown but could be related to in vivo versus in vitro IL-12 exposure and the different source of the target cells (spleen versus umbilical cord blood, mouse versus human, etc.).

IL-12 administration at birth also increased neonatal B cell responsiveness. Specifically, mice primed at birth with antigen and IL-12, and boosted as adults with homologous antigen showed dramatic enhancement of IgG1, IgG2a and IgG2b antibody levels compared to mice exposed to antigen only as adults. These results were obtained using two different model protein antigens and two different adjuvants. The ability of IL-12 to alter the isotype restricted antibody response of adult mice to HEL has been previously shown (Buchanan, J. M., et al., *Int. Immunol.*, 7:1519–1528 (1995)). Specifically, parenteral injections of IL-12 plus HEL greatly elevated HEL-specific serum IgG2a and temporarily suppressed IgG1 antibody production. In addition, others (McKnight, A. J., et al., *J. Immunol.*, 152:2172–2179 (1994); Morris, S. C., et al., *J. Immunol.*, 152:1047–1056 (1994); Germann, T., et al., *Eur. J. Immunol.*, 25:823–829 (1995); Wynn, T. A., et al., *J. Immunol.*, 157:4068–4078 (1996)) have demonstrated that IL-12 administration enhances serum IgG2a, IgG2b and IgG3 antibody responses to protein antigens. Thus, the effects of IL-12 on adult humoral immunity are well established. The results described herein show that newborn mice respond to IL-12 treatment in a similar fashion by redirecting antibody responses towards a Th1 profile with enhancement of IgG2a and IgG2b antibodies. Murine antibodies of the IgG2a isotype are known to be very efficient at opsonization and complement fixation, and that fact that IL-12 enhances this isotype is particularly useful in neonatal immunization strategies that involve such protection mechanisms.

Due to the Th2 bias of the normal newborn immune system and the unique vulnerability of neonates to infectious agents, there has been continual interest in developing immunization strategies and adjuvants that stimulate Th1 immunity (Van Regenmortel, M., *ASM News*, 63:136–139 (1996)). Adjuvants currently acceptable for human use such as alum lack the capacity to generate cell-mediated immune (Th1) responses which are an essential component of host defense against a variety of pathogens (Gupta, R. K., et al., *Novel Strategies in Design and Production of Vaccines*, eds. Cohen, S. & Shafferman, A. (Plenum Press, New York), pp. 105–113). Recently, Martinez et al. (Martinez, X., et al., *Proc. Natl. Acad. Sci., USA*, 94:8726–8731 (1998)) demonstrated that immunization of newborn mice with DNA-based vaccines resulted in the induction of Th1 immune responses characterized by enhanced IFN-γ and IgG2a production. DNA vaccination of newborn animals with a plasmid expressing influenza hemagglutinin has also been shown to induce Th1 responses and to confer protection against a lethal challenge of influenza virus (Bot, A., et al., *Int. Immunol.*, 9:1641–1650 (1998)). In addition, it has been shown that immunization with antigen plus synthetic oligodeoxynucleotides with CpG motifs induces Th1 responses through stimulation of IL-12 production (Chu, R. S., et al., *J. Exp. Med.*, 186:1623–1631 (1997)). Therefore, IL-12 administration is a powerful and direct method for stimulating neonatal immunity in humans.

Neonatal animals show generally poor responsiveness to foreign antigens and are known to display polarized expression of Th2-like cytokines and antibody responses. As described herein, newborn mice are deficient in peripheral expression of the Th1-inducing cytokine, IL-12. Attempts to overcome this deficiency by immunization and treatment with IL-12 at birth resulted in elevated levels of IFN-γ and IL-10 mRNA in the spleens of mice compared to animals exposed to antigen only. Moreover, such animals showed dramatic enhancement of IgG2a and IgG2b antibody levels upon adult challenge compared to mice primed with antigen alone. IgG1 antibody levels, a measure of Th2 activity, were unaffected or even somewhat enhanced by neonatal IL-12 treatment. Taken together, these results provide the first evidence that IL-12 administration induces a Th1-like cytokine response in newborns and causes priming for heightened memory responses in vivo. The findings described herein demonstrate that IL-12 can be used as a vaccine adjuvant in neonates for inducing protection against common childhood pathogens.

Thus, the methods and described herein can be used to treat and/or prevent a disease or condition associated with a pathogen having one or more antigens in a neonatal host. The methods described herein can utilize an effective amount of IL-12 in combination with a single antigen or multiple antigens which can be derived from the same pathogen, from different strains of a pathogen or from different pathogens. Thus, IL-12 and one or more antigens can be used to prevent and/or treat one or more disease or condition associated with the pathogen(s) from which the antigen(s) is derived.

The present invention is illustrated by the following examples, which are not intended to be limiting in any way.

EXEMPLIFICATION

Materials and Methods

Mice

BALB/c mice were obtained from the National Cancer Institute (Bethesda, Md.) at 4 to 6 weeks of age and bred at the Medical College of Ohio. Food and water were provided ad libitum. Animal care and experimental procedures were in compliance with the Institutional Animal Care and Use Committee (IACUC) of the Medical College of Ohio.

Neonatal immunization protocol

One day-old mice were injected intraperitoneally (i.p.) with 100 μg of DNP-OVA (Biosearch Technologies, San Raphael, Calif.) or 100 μg HEL. The antigens were emulsified in incomplete Freund's adjuvant (IFA; Life Technologies, Gaithersburg, Md.) according to the method of Forsthuber et al., *Science*, 271:1728–1730 (1996), or mixed with 2 mg/ml of alum (Rehydrogel Low Viscosity Gel, Reheis, Inc., Berkeley Heights, N.J.) and the total injection volume was 25 μl/mouse. Experimental mice were injected i.p. on day 1 with 1 μg of recombinant murine IL-12 that was diluted in PBS containing 1% normal BALB/c mouse serum (PBS-NMS); control mice received only PBS-NMS. The mice were allowed to mature to adulthood and then at 5–6 weeks of age, they were boosted with the same amount of antigen emulsified in complete Freund's adjuvant (CFA; Gibco-BRL) or alum. The mice were bled at weekly intervals from the retro-orbital plexus. In the case of in utero treatments, pregnant mice were injected subcutaneously with the same amounts of antigen in alum +/−IL-12 approximately 7 days before giving birth.

RNA isolation

Total RNA isolation from snap frozen spleens, livers, and thymuses from 3 day-old mice was performed with Trizol reagent (Gibco-BRL Gaithersburg, Mass.) according to the manufacturer's instructions. Briefly, the frozen tissues were homogenized with a mortar and pestle, and immediately transferred into polystyrene tubes containing 1 ml of Trizol reagent. The homogenized samples were incubated for 5 minutes at room temperature to allow dissociation of the nucleoprotein complexes and centrifuged at 12,000 g for 10 minutes at 4° C. The supernatant fluids were then mixed for 15 seconds with 0.2 ml of chloroform, incubated for 15 minutes on ice, and centrifuged at 12,000 g for 15 minutes at 4° C. Following centrifugation, the RNA in the aqueous phase was precipitated at −20° C. for one hour by the addition of 1.0 ml isopropanol. The samples were centrifuged for 15 minutes at 12,000 g and the RNA pellet was washed twice with 1.0 ml of 75% ethanol. The pellets were air-dried for 2–5 minutes, solubilized in DEPC-treated water, and stored at −80° C. The concentration of total RNA was calculated using the A260 value for single-stranded RNA (1 A260 unit=40 μg of single-stranded RNA/ml). The final preparation of total RNA yielded a 260/280 ratio of 1.7–2.0.

First strand cDNA synthesis

First strand cDNA synthesis was carried out following the manufacturer's instructions (Gibco-BRL). Briefly, 1 μg of oligo(dT), 3 μg of total RNA, and sterile DEPC-treated water were added to an eppendorf tube to a final volume of 11 μl. The mixture was incubated at 70° C. for 10 minutes and then chilled on ice. Subsequently, the following components were added in order: 4.0 μl of 5× first strand buffer, 2 μl of 0.1 M DTT, and 1 μl of dNTP mixture (10 mM each of dATP, dGTP, dCTP, and dTTP). The contents of the tube were mixed gently and incubated at 42° C. for 2 minutes, followed by the addition of 1 μl (200 U) of Superscript II reverse transcriptase (RT). The reaction mixture was gently mixed and incubated at 42° C. for one hour. The reaction was then terminated by incubation at 70° C. for 15 minutes.

Polymerase Chain Reaction (PCR)

A 50 μl reaction mixture was prepared in a sterile eppendorf tube with the following components: 31.3 μl DEPC treated water, 10.0 μl of 5× Tris-HCL buffer (optimal magnesium and pH were determined for each primer set), 2 μl of cDNA from the first strand synthesis, 2 μl primer (20 μm stock concentration), 5.0 μl of dNTP mix (2.5 mM dATP, 2.5 mM dCTP, 2.5 mM dGTP, and 2.5 mM dTTP, pH 8.0) (Invitrogen Corporation), and 0.5 μl (2.5 U) of Taq DNA polymerase (Gibco-BRL). The tubes were placed into the wells of a Perkin Elmer Thermal Cycler 480 (Perkin Elmer Cetus, Norwalk, Conn.), incubated at 95° C. for 5 minutes and then subjected to the following amplification profile: 1 minute at 95° C., 1 minute at 56° C. and 1 minute at 72° C. for a duration of 35 cycles. This was followed by incubation at 72° C. for 10 minutes followed by a soak cycle at 4° C. The PCR products were separated on a 2.5% agarose gel and stained with ethidium bromide. The bands were visualized and photographed using UV transillumination. Hypoxanthine phosphoribosyl transferase (HPRT) was used as a housekeeping control to ensure equal loading of RNA in all lanes and a 100 bp DNA ladder (Gibco-BRL) was used as a molecular weight marker.

Primer sequences:

Detection of antibody and isotype levels by ELISA

Anti-DNP and anti-HEL antibody levels were determined by isotype-specific ELISA as described (Buchanan, J. M. et. al., *Int. Immunol.*, 7:1519–1528 (1995) and Metzger, D. W. et. al., *Eur. J. Immunol.*, 27:1958–1965 (1997)). Briefly, microtiter plates (Nalge Nunc International, Rochester, N.Y.) were coated overnight with 10 μg/ml DNP-bovine serum albumin (BSA) or 100 μg/ml of HEL in PBS. The plates were washed with PBS containing 0.1% (w/v) gelatin and 0.05% (v/v) Tween 20. Serial dilutions of serum were then added and the plates were incubated for 2 hours at room temperature. The plates were again washed and incubated for 1 hour with goat anti-mouse IgG1, IgG2a or IgG2b conjugated to alkaline phosphatase (Southern Biotechnology Associates, Birmingham, Ala.). The plates were washed and p-nitrophenyl phosphatase substrate was added to obtain optimal color development. The plates were read at 405 nm with an ELISA microplate reader (Bio-Tek Instruments, Winooski, Vt.). Anti-HEL antibodies were measured in a similar manner except that the plates were coated with 100 μg/ml of HEL as described (Buchanan, J. M., et al., *Int. Immunol.*, 7:1519–1528 (1995). In all cases, appropriate working dilutions and isotype specificities of the secondary antibody conjugates were determined using purified myeloma proteins of known isotype (Sigma, St. Louis, Mo.). The antigen specificity of the assays was established using plates coated with BSA. Statistical analyses were performed using the Mann-Whitney U test. Data were considered statistically significant if p values were <0.05.

RESULTS

Neonatal mice are deficient in the expression of IL-12 in the spleen

RT-PCR was performed to examine IL-12 p40 mRNA expression in three day-old and adult mice that had been immunized two days previously with DNP-OVA. Neonatal mice that received PBS-NMS only, antigen only or antigen plus IL-12 were found to uniformly lack expression of IL-12 p40 mRNA in the spleens. Conversely, adult mice that received PBS-NMS only or antigen only did express IL-12 p40 mRNA in the spleens which was further enhanced by IL-12 treatment.

```
HPRT
5' GTT GGA TAC AGG CCA GAC TTT GTT G 3'      (SEQ ID NO: 1)

5+ GAT TCA ACT TGC GCT CAT CTT AGG C 3'      (SEQ ID NO: 2)

IL-4
5' GTT GTC ATC CTG CTC TTC TTT 3'            (SEQ ID NO: 3)

5' CTC TCT GTG GTG TTC TTC GTT 3'            (SEQ ID NO: 4)

IL-5
5' GAC AAG CAA TGA GAC GAT GAG 3'            (SEQ ID NO: 5)

5' GTT ATC CTT GGC TAC ATT ACC 3'            (SEQ ID NO: 6)

IL-10
5' ATG CAG GAC TTT AAG GGT TAC TTG GGT T 3'  (SEQ ID NO: 7)

5' ATT TCG GAG AGA GGT ACA AAC GAG GTT T 3'  (SEQ ID NO: 8)

IL-12 p40
5' CTC ACA TCT GCT GCT CCA CAA 3'            (SEQ ID NO: 9)

5' CTC CTT CAT CTT TTC TTT CTT 3'            (SEQ ID NO: 10)

IFN-γ
5' TGA ACG CTA CAC ACT GCA TCT TGG 3'        (SEQ ID NO: 11)

5' CGA CTC CTT TTC CGC TTC CTG AG 3'         (SEQ ID NO: 12)
```

In contrast to the results obtained above, there was clear expression of IL-12 p40 mRNA in the thymuses of unimmunized neonatal mice and neonatal mice exposed to antigen. In addition, there was significant enhancement of IL-12 p40 mRNA expression in the thymuses after IL-12 inoculation. Adult mice immunized in the same fashion exhibited a similar pattern of IL-12 expression in the thymuses. Simultaneous amplification of HPRT mRNA confirmed that equal amounts of RNA were utilized in each RT-PCR reaction. These results show that neonates fail to produce IL-12 in a peripheral lymphoid organ, although they are able to express it in the thymus, a primary lymphoid organ. IL-12 induces a Th1-like cytokine response in neonatal mice To further characterize the unique features of neonatal immune responses, IFN-γ and IL-10 mRNA expression after exposure to DNP-OVA or HEL was examined. It was found that mice which received PBS-NMS or antigen did not express appreciable levels of IFN-γ or IL-10 mRNA in the spleens. However, mice that were immunized with DNP-OVA or HEL simultaneously treated with IL-12 did exhibit significant induction of IFN-γ and IL-10 mRNA expression. Both IFN-γ and IL-10 are known to be induced in adult mice by IL-12 treatment (Gerosa, F., et al., *J. Exp. Med.*, 183:2559–2569 (1996); Sher, A., et al., *Ann. N.Y. Acad. Sci.*, 795:202–207 (1996)) and analysis of adult splenic mRNA in the experiments revealed the expected results. Notably, and in contrast to neonatal mice, treatment of adults with antigen only did induce low but detectable levels of IFN-γ mRNA in the spleens. These results demonstrate the ability of IL-12 to modulate antigen-driven cytokine responses in neonatal mice in a manner similar to that observed in adult mice, resulting in significant enhancement of IFN-γ and IL-10 mRNA expression.

Figure 1B:
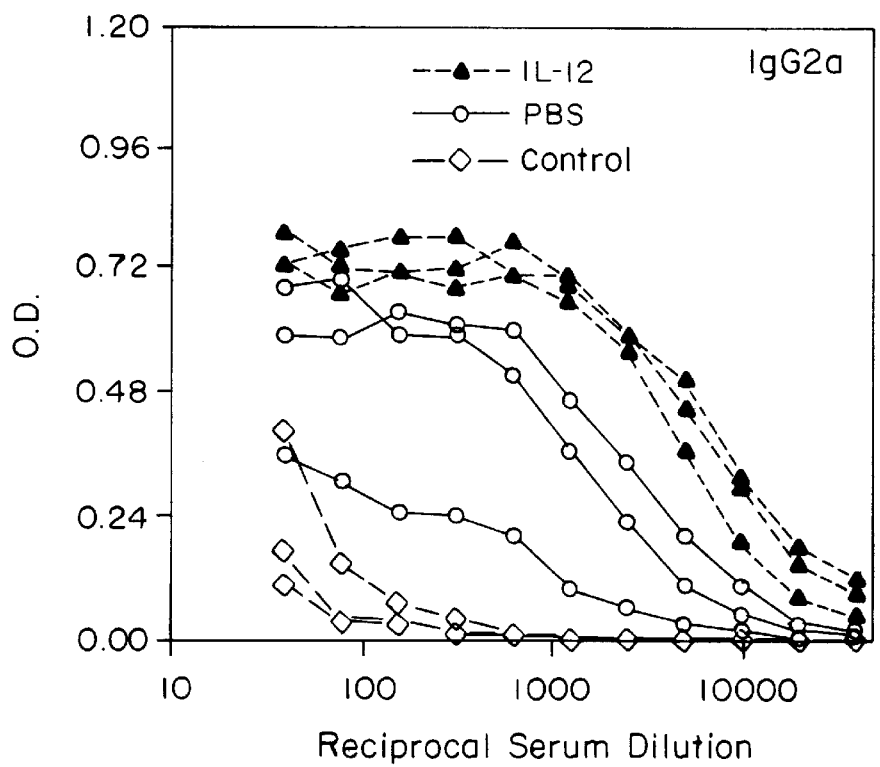
Figure 1C:
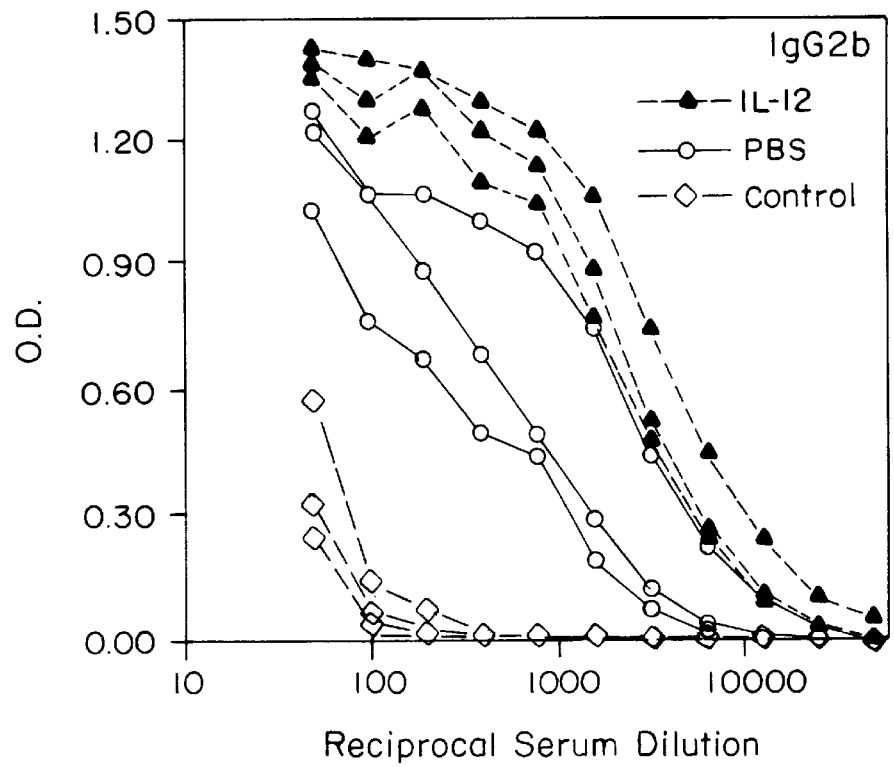

Mice primed with antigen and IL-12 at birth exhibit a Th1-like serum antibody response The effects of IL-12 on B cell priming were determined by boosting neonatally-treated adult mice with antigen in CFA and measuring antibody levels by isotype-specific ELISA. Mice that were immunized at birth with DNP-OVA and then boosted with homologous antigen as adults showed elevated IgG1, IgG2a and IgG2b antibody levels compared to animals exposed to antigen only as adults (FIGS. 1A–1C). Thus, neonatal immunization of DNP-OVA caused priming of mice for an enhanced anti-DNP antibody response upon adult challenge, a finding which confirmed the results of Forsthuber, T. et. al., *Science*, 271:1728–1730 (1996). Animals treated at birth with antigen plus IL-12 showed even more dramatic enhancement of IgG2a and IgG2b antibody levels upon adult challenge compared to mice primed with antigen alone. However, there were no differences in IgG1 antibody levels between mice inoculated with antigen and IL-12 and those inoculated with antigen alone (control groups).

Figure 1D:
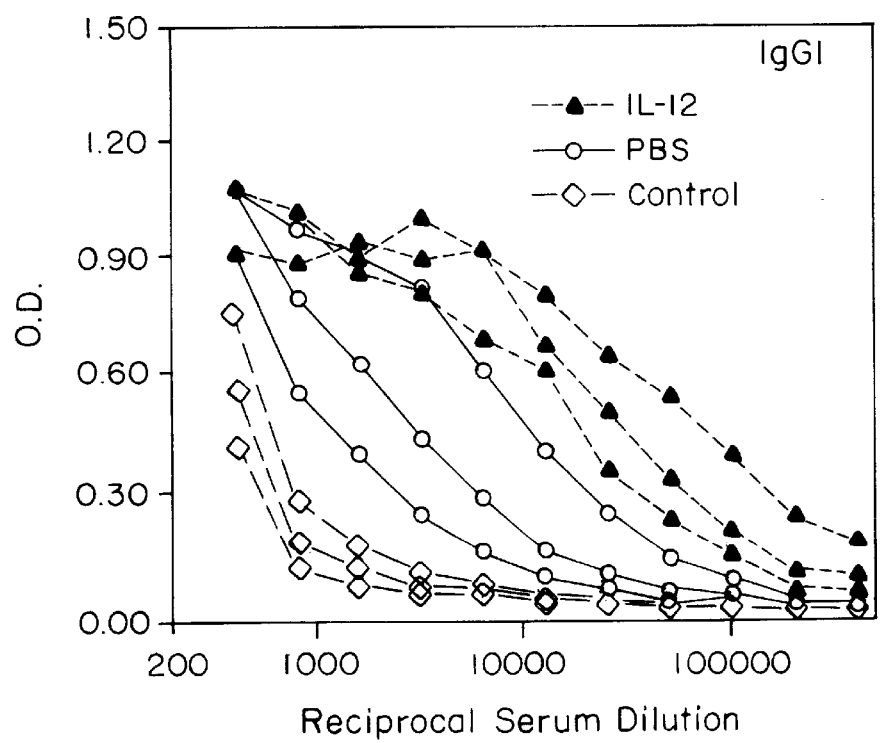
FIGS. 1D–1F are graphs of reciprocal serum dilution versus O.D. showing the effects of IL-12 on serum anti-hen eggwhite lysozyme (HEL) levels after HEL priming +/–IL-12 in mice injected with HEL in IFA plus IL-12 (closed triangles), HEL in IFA plus PBS vehicle (open circles) or PBS vehicle only (open squares); each line represents binding of serum from an individual mouse; the mice were then challenged after 5–6 weeks of age with HEL in CFA and the sera were tested 7 days later for anti-HEL antibodies by ELISA; the differences in binding between mice primed with HEL and IL-12 and those primed with HEL and PBS were significant at $p<0.05$ for IgG1.
Figure 1E:
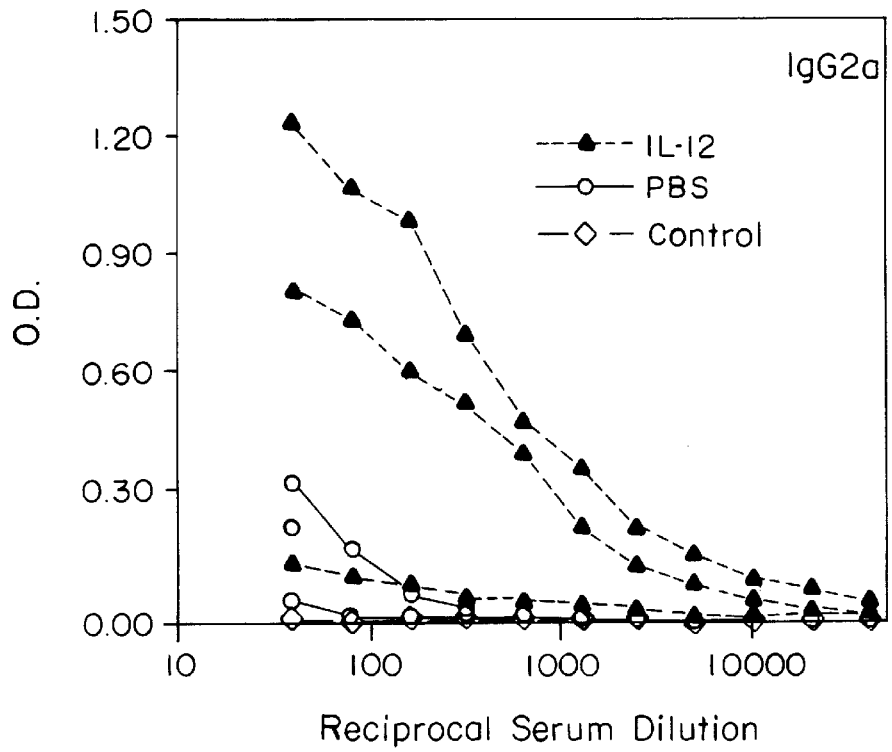
Figure 1F:
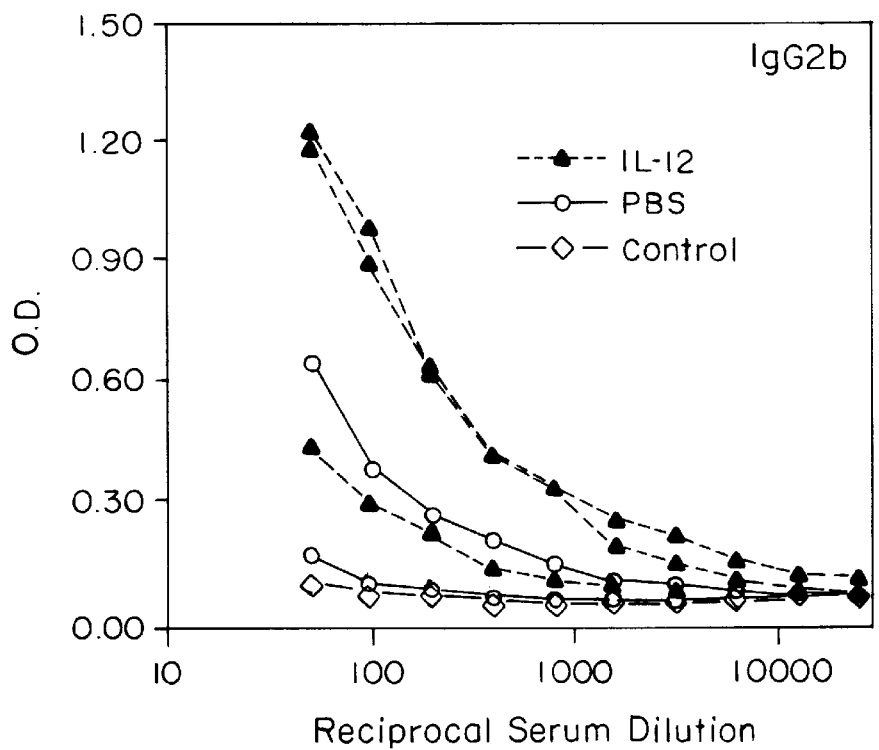

The results were confirmed using another model antigen, HEL, that in adult mice normally induces an IgG1 isotype-restricted response which can be dramatically skewed by IL-12 administration (Buchanan, J. M., et al., *Int. Immunol.*, 7:1519–1528 (1995)). Mice challenged with HEL as adults but not primed at birth showed low IgG1 responses which were enhanced by neonatal priming (FIGS. 1D–1F). There was little IgG2a or IgG2b produced in either case, in keeping with previous work (Buchanan, J. M., et al., *Int. Immunol.*, 7:1519–1528 (1995)). However, two of three mice that were primed at birth with HEL and IL-12 developed strong IgG2a and IgG2b antibody responses upon adult challenge. Furthermore, there was a enhancement of IgG1 antibody production in IL-12 treated mice, again in agreement with previous findings showing that IL-12 can enhance IgG1 antibody levels in adult mice after an initial suppressive phase (Buchanan, J. M., et al., *Int. Immunol.*, 7:1519–1528 (1995); Metzger, D. W., et al., *Ann. N.Y. Acad. Sci.*, 795:100–115 (1996)). IgG3 serum antibody levels were not detectable after immunization with either DNP-OVA or HEL.

Figure 2A:
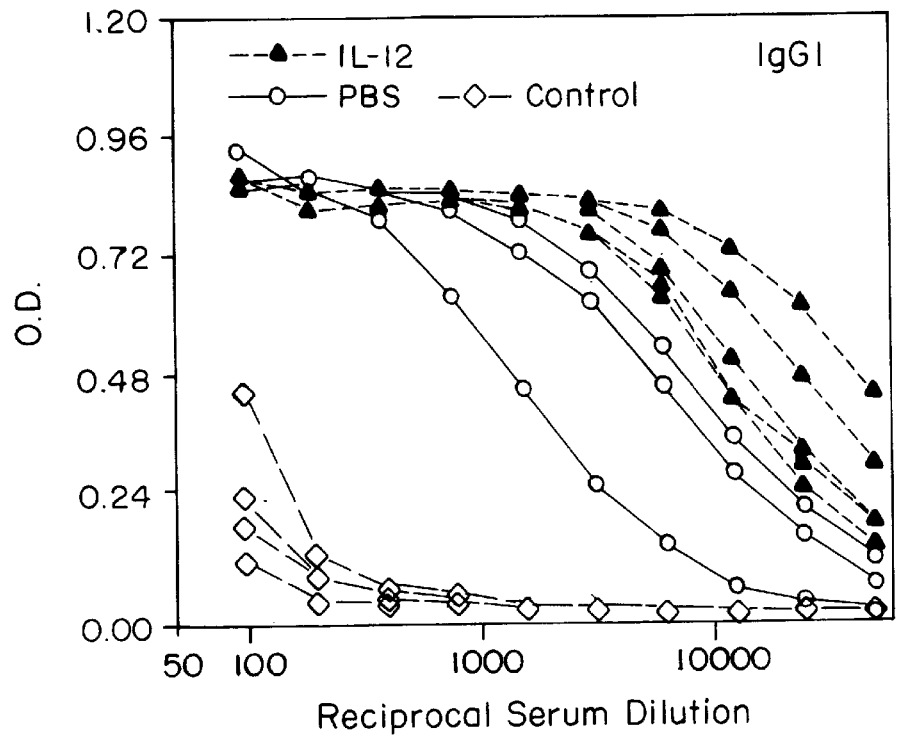
FIGS. 2A–2C are graphs of reciprocal serum dilution versus O.D. showing the effects of IL-12 on serum anti-DNP levels after neonatal DNP-OVA priming +/–IL-12 in mice injected with DNP-OVA in alum plus IL-12 (closed triangles), DNP-OVA in either alum plus PBS vehicle (open circles) or PBS vehicle only (open squares); each line represents binding of serum from an individual mouse; the mice were then challenged after 5–6 weeks of age with DNP-OVA in CFA and the sera were tested 7 days later for anti-DNP antibodies by ELISA; the differences in binding between mice primed with DNP-OVA and IL-12 and those primed with DNP-OVA and PBS were significant at $p<0.05$ for all isotypes.
Figure 2B:
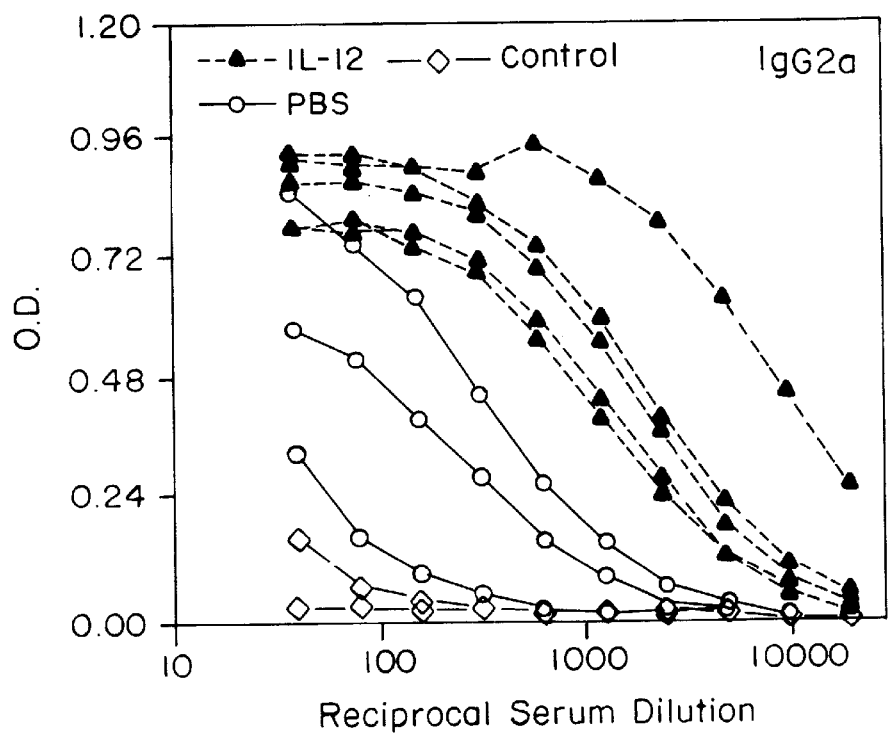
Figure 2C:
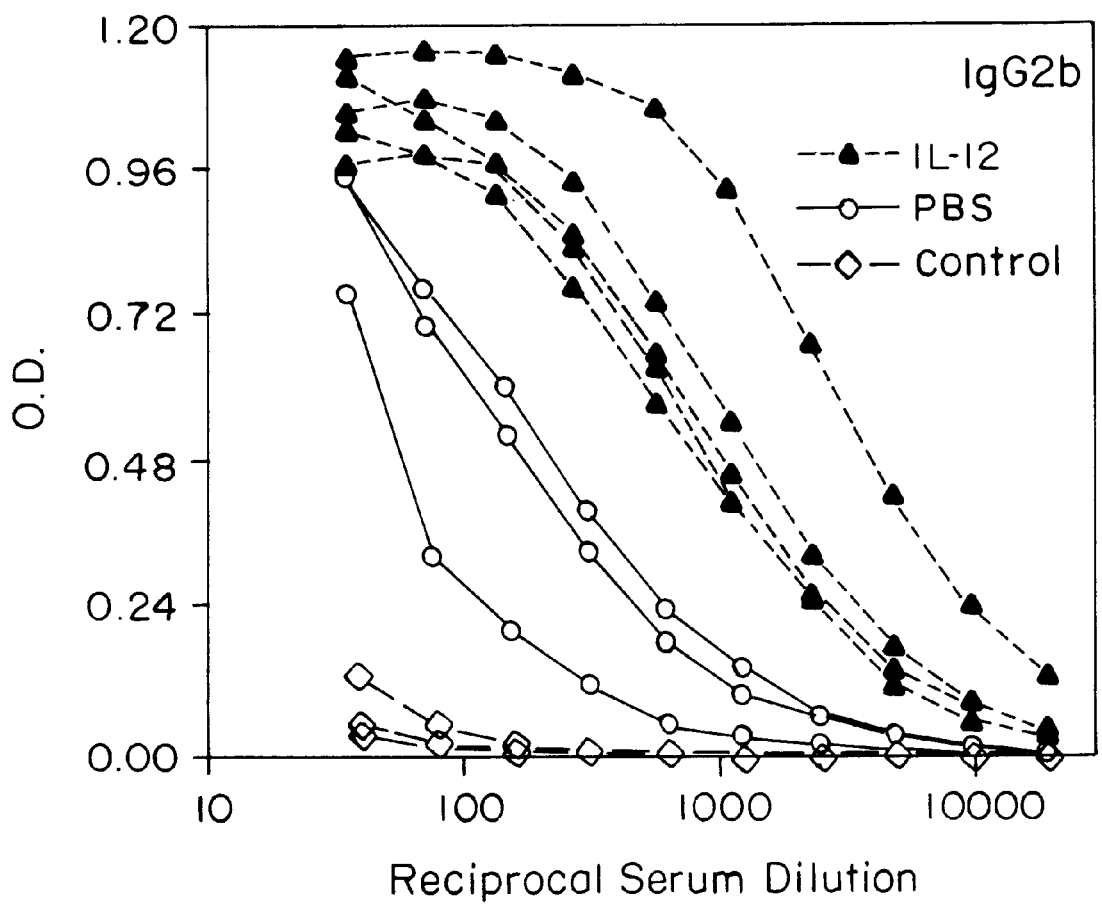

Since Freund's adjuvant is highly inflammatory and restricted to animal use, experiments using DNP-OVA precipitated in alum, an approved human adjuvant, were conducted. The results obtained with alum were even more impressive that those observed after priming with IFA (FIGS. 2A–2C). Animals treated with antigen plus IL-12 exhibited a significant increase in IgG2a and IgG2b levels compared to mice primed with antigen alone. Furthermore, there was an enhancement of IgG1 antibody levels in IL-12 treated mice compared to mice immunized with antigen alone.

Effects of IL-12 on serum anti-DNP levels after in utero DNP-OVA priming +/−IL-12

Figure 3A:
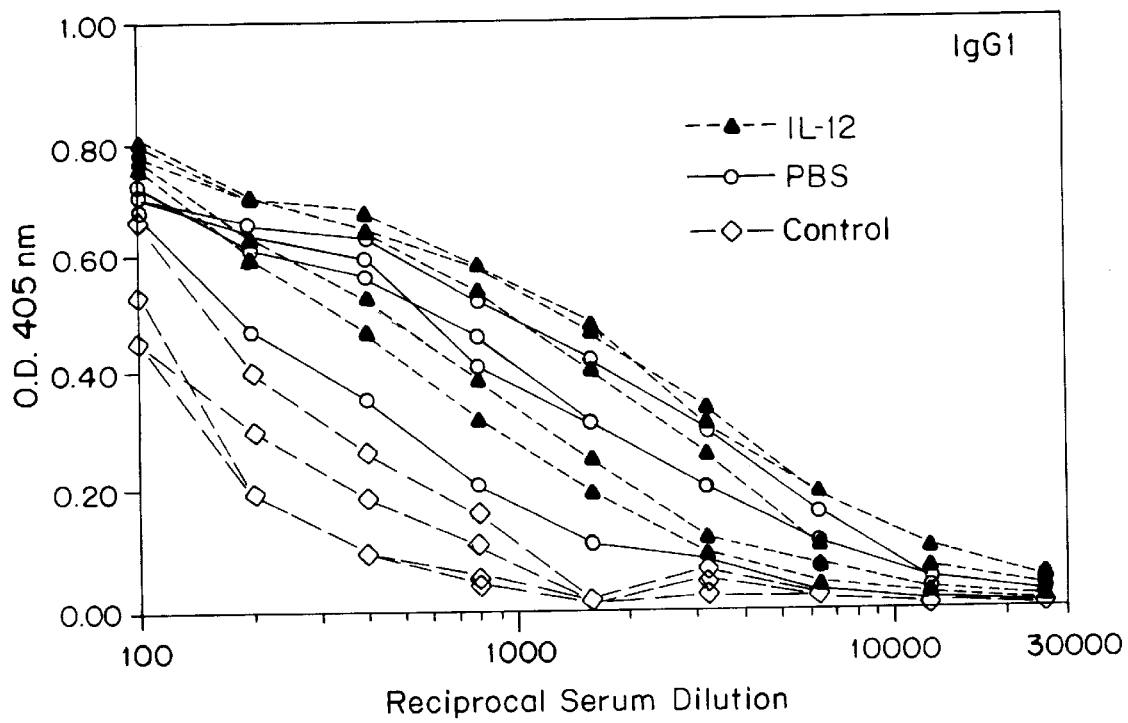
FIG. 3A-3B are graphs of reciprocal serum dilution versus O.D. 405 nm showing the effects of injecting pregnant mice subcutaneously with either DNP-OVA in alum plus IL-12 (closed triangles), DNP-OVA in either alum plus PBS vehicle (open circles), or PBS vehicle only (open diamonds); mice which were born were then challenged after 9–10 weeks of age with DNP-OVA in alum and the sera were tested 7 days later for anti-DNP antibodies by ELISA; each line represents binding of serum from an individual mouse.
Figure 3B:
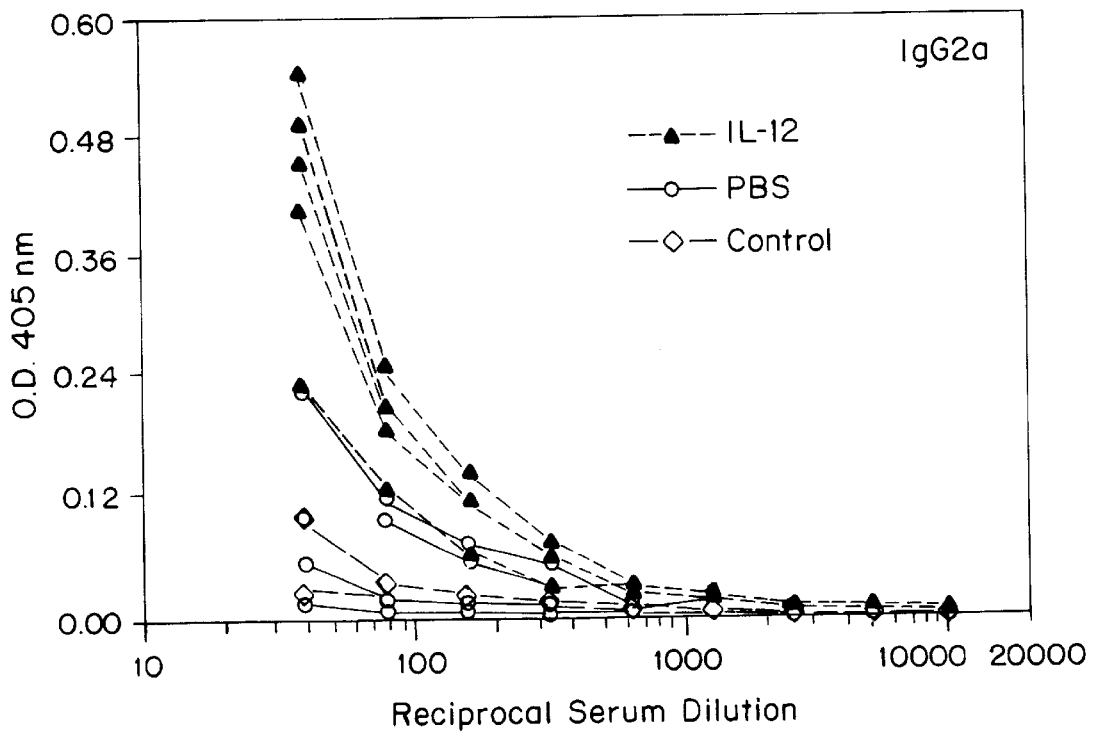

Pregnant mice were injected subcutaneously with either DNP-OVA in alum plus IL-12, DNP-OVA in alum plus PBS vehicle, or PBS vehicle only. Mice which were born were then challenged after 9–10 weeks of age with DNP-OVA in alum and the sera were tested 7 days later for anti-DNP antibodies by ELISA. See FIGS. 3A-3B. The results showed dramatic increases in IgG2a anti-DNP antibody levels in mice born to mothers that were treated with DNP-OVA and IL-12. There was little if any effect on IgG1 antibody levels.

Therefore, IL-12 has effects on humoral immunity that are similar in both neonates and adults. The findings described herein show that IL-12 administered at birth is capable of inducing strong Th1-type cytokine and antibody responses to T-dependent antigens. Since neonatal responses to various vaccine antigens are biased towards a Th2 pattern (Forsthuber, T., et al., *Science*, 271:1728–1730 (1996); Adkins, B., et al., *J. Immunol.*, 153:3378–3385 (1994); Coutinho, G., et al., *Eur. J. Immunol.*, 24:1858–1862 (1994); Early, E. M., et al., *Eur. J. Immunol.*, 26:2885–2889 (1996); Barrios, C., et al., *Eur. J. Immunol.*, 26:1489–1496 (1996); Kobayashi, M., et al., *J. Exp. Med.*, 170:827–845 (1989)), IL-12 administration is an effective adjuvant in childhood immunization strategies.

Expression of IFN-γ and IL-10 mRNA in the spleens of neonatal mice

Neonatal mice were injected i.p. on day 1 with HANA in alum plus IL-12 or PBS vehicle. Control mice received only PBS vehicle without antigen. Mice were sacrificed 2 days after treatment, and total RNA was isolated from 3–4 pooled neonatal spleens. Expression of IFN-γ (459 bp), IL-10 (455 bp) and HPRT (162 bp) was assayed by RT-PCR.

IL-12 p40 mRNA expression in the spleens and thymuses of neonatal and adult mice Mice were injected i.p. on day 1 with HANA in alum plus IL-12 or PBS vehicle. Control mice received only PBS vehicle without antigen. Mice were sacrificed 2 days after treatment, and total RNA was isolated from 3–4 pooled neonatal spleens and thymuses. Expression of IL-12 p40 (525 bp) and HPRT (162 bp) was assayed by RT-PCR.

Effects of IL-12 on serum anti-purified hemagglutinin and neuraminidase derived from influenza virus (HANA) levels after neonatal HANA priming +\−IL-12

Figure 4A:
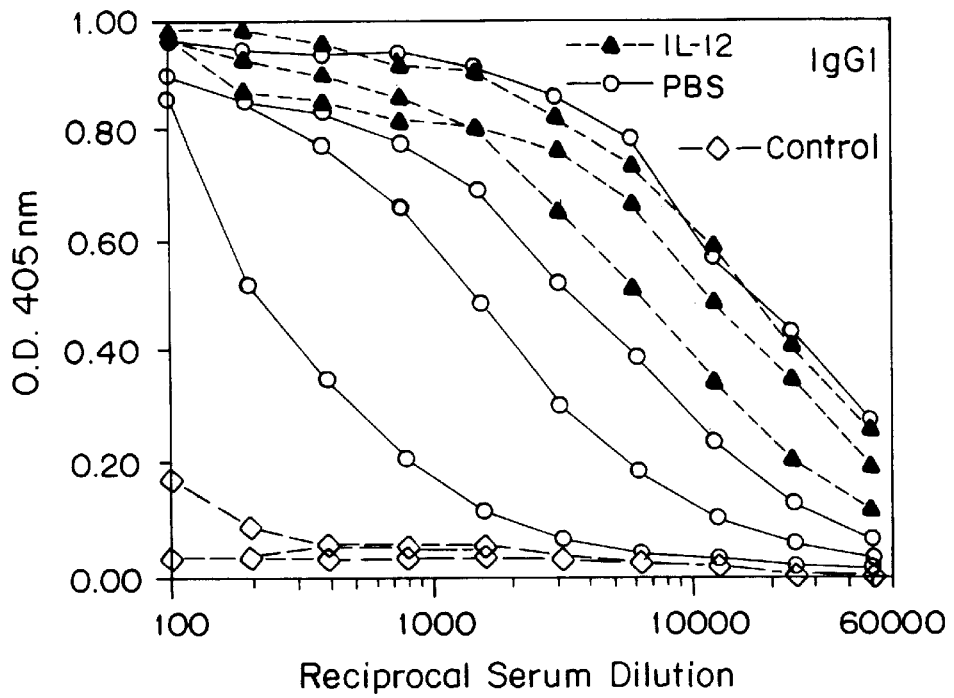
FIGS. 4A-4B are graphs of reciprocal serum dilution versus O.D. 405 nm showing the effects of IL-12 on serum anti-purified hemagglutinin and neuraminidase derived from influenza virus (HANA) levels after neonatal HANA priming +\–IL-12; mice were injected on day 1 with either HANA in alum plus IL-12 (closed triangles), HANA in alum plus PBS vehicle (open circles), or PBS vehicle only (open squares); all mice were then challenged at 5–6 weeks of age with HANA in alum and the sera were tested 7 days later for anti-HANA antibodies by ELISA; each line represents binding of serum from an individual mouse.
Figure 4B:
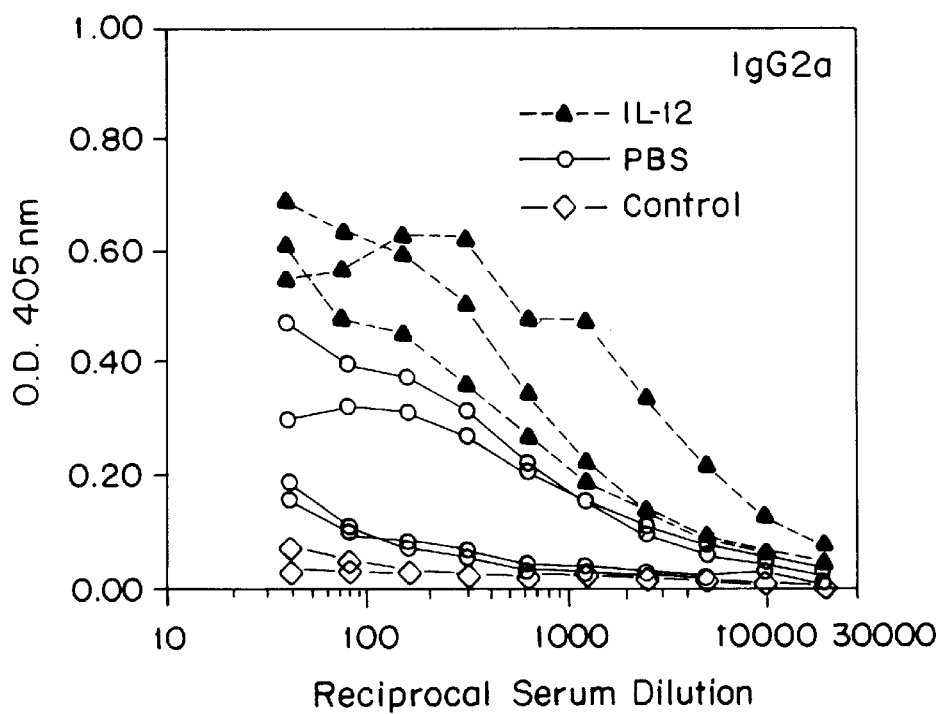

The effects of IL-12 on serum anti-HANA levels after neonatal HANA priming+\−IL-12 were examined. Mice were injected on day 1 with either HANA in alum plus IL-12, HANA in alum plus PBS vehicle, or PBS vehicle only. All mice were then challenged at 5–6 weeks of age with HANA in alum and the sera were tested 7 days later for anti-HANA antibodies by ELISA; each line represents binding of serum from an individual mouse. See FIGS. 4A-4B.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A method of inducing an immune response to a pathogen in a neonatal host and priming the host for a memory response to the pathogen as an adult, which comprises administering to the neonatal host an effective amount of interleukin-12 and an antigen of the pathogen.

2. The method of claim 1 wherein the pathogen is selected from the group consisting of: bacteria, viruses, parasites, fungi and yeasts.

3. The method of claim 2 wherein the bacteria is selected from the group consisting of: bacillus, Group B streptococcus, Bordetella, Listeria, *Bacillus anthracis, S. pneumoniae, N. meningiditis* and *H. influenza.*

4. The method of claim 1 wherein the immune response is a cytokine response.

5. The method of claim 4 wherein the cytokine response results in an expression of interferon-γ and interleukin-10 in the host compared to a host which did not receive the effective amount of IL-12 and the antigen of the pathogen.

6. The method of claim 1 wherein the immune response is a humoral immune response.

7. The method of claim 6 wherein the humoral immune response results in an expression of IgG1, IgG2a and IgG2b antibody levels in the host compared to a host which did not receive the effective amount of IL-12 and the antigen of the pathogen.

* * * * *

```
                           SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
              (A) LENGTH: 25 base pairs
              (B) TYPE: nucleic acid
              (C) STRANDEDNESS: single
              (D) TOPOLOGY: linear (ii) MOLECULE TYPE: other nucleic acid
              (A) DESCRIPTION: /desc = "DNA"

(xi) SEQUENCE DESCRIPTION: SEQ ID NO:1:

GTTGGATACA GGCCAGACTT TGTTG                                             25

(2) INFORMATION FOR SEQ ID NO:2:

(i) SEQUENCE CHARACTERISTICS:
              (A) LENGTH: 25 base pairs
              (B) TYPE: nucleic acid
              (C) STRANDEDNESS: single
              (D) TOPOLOGY: linear (ii) MOLECULE TYPE: other nucleic acid
              (A) DESCRIPTION: /desc = "DNA"

(xi) SEQUENCE DESCRIPTION: SEQ ID NO:2:

GATTCAACTT GCGCTCATCT TAGGC                                             25

(2) INFORMATION FOR SEQ ID NO:3:

(i) SEQUENCE CHARACTERISTICS:
              (A) LENGTH: 21 base pairs
              (B) TYPE: nucleic acid
              (C) STRANDEDNESS: single
              (D) TOPOLOGY: linear (ii) MOLECULE TYPE: other nucleic acid
              (A) DESCRIPTION: /desc = "DNA"

(xi) SEQUENCE DESCRIPTION: SEQ ID NO:3:

GTTGTCATCC TGCTCTTCTT T                                                 21

(2) INFORMATION FOR SEQ ID NO:4:

(i) SEQUENCE CHARACTERISTICS:
              (A) LENGTH: 21 base pairs
              (B) TYPE: nucleic acid
              (C) STRANDEDNESS: single
              (D) TOPOLOGY: linear (ii) MOLECULE TYPE: other nucleic acid
              (A) DESCRIPTION: /desc = "DNA"

(xi) SEQUENCE DESCRIPTION: SEQ ID NO:4:
```

CTCTCTGTGG TGTTCTTCGT T                                          21

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:5:

GACAAGCAAT GAGACGATGA G                                          21

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:6:

GTTATCCTTG GCTACATTAC C                                          21

(2) INFORMATION FOR SEQ ID NO:7:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:7:

ATGCAGGACT TTAAGGGTTA CTTGGGTT                                   28

(2) INFORMATION FOR SEQ ID NO:8:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:8:

ATTTCGGAGA GAGGTACAAA CGAGGTTT                                   28

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:9:

-continued

```
CTCACATCTG CTGCTCCACA A                                          21

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:10:

CTCCTTCATC TTTTCTTTCT T                                          21

(2) INFORMATION FOR SEQ ID NO:11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:11:

TGAACGCTAC ACACTGCATC TTGG                                       24

(2) INFORMATION FOR SEQ ID NO:12:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:12:

CGACTCCTTT TCCGCTTCCT GAG                                        23
```